United States Patent [19]

Coan et al.

[11] 4,379,087

[45] Apr. 5, 1983

[54] METHOD OF PREPARING ALPHA-1-PROTEINASE INHIBITOR

[75] Inventors: Michael H. Coan, El Cerrito; William J. Brockway, San Leandro, both of Calif.

[73] Assignee: Cutter Laboratories, Inc., Berkeley, Calif.

[21] Appl. No.: 389,202

[22] Filed: Jun. 17, 1982

[51] Int. Cl.³ .............................................. C07G 7/00
[52] U.S. Cl. ................................ 260/112 B; 424/101
[58] Field of Search ...................... 260/112 B; 424/101

[56] References Cited

U.S. PATENT DOCUMENTS 3,415,804  12/1968  Polson .............................. 260/112 B

OTHER PUBLICATIONS

Biochemistry, vol. 13, pp. 5439–5445, Pannell et al., (1974).
Biochem. J., vol. 157, pp. 339–351 (1976), Saklatvala et al.
Biochemistry, vol. 15, pp. 798–804 (1976), Musiani et al.
Preparative Biochemistry, vol. 3, No. 6, pp. 541–552 (1973), Kress et al.
Preparative Biochemistry, vol. 5, No. 4, pp. 333–348 (1975), Glaser et al.

Primary Examiner—Howard E. Schain
Attorney, Agent, or Firm—Theodore J. Leitereg

[57] ABSTRACT

A method is disclosed for separating alpha-1-proteinase inhibitor from a blood plasma fraction particularly from the Cohn fractionation scheme. An aqueous solution of the blood plasma fraction is held at a pH of about 6.5–8.5, and a temperature of about 2°–50° C. for a period of about 0.2–24 hours and then mixed with a poly-condensed polyglycol in a proportion of about 10–15 parts of polymer per 100 ml of aqueous solution containing the blood plasma fraction. The mixture may be held at a temperature of about 2°–10° C. for a period of about 1–24 hours. Next, the pH of the mixture is adjusted to about 4.6–5.7, to selectively precipitate unwanted proteins from the solution of alpha-1-proteinase inhibitor which is separated from the solution and purified further.

16 Claims, No Drawings

METHOD OF PREPARING ALPHA-1-PROTEINASE INHIBITOR

BACKGROUND OF THE INVENTION

1. Field of the Invention

This invention relates to and has among its objects the provision of a novel method for separating alpha-1-proteinase inhibitor (PI) from blood plasma or blood plasma fractions. Further objects of the invention will be evident from the following description wherein parts and percentages are by weight unless otherwise specified.

2. Description of the Prior Art

Alpha-1-proteinase inhibitor is a glycoprotein having molecular weight of 54,000. The protein consists of a single polypeptide chain to which several oligosaccharide units are covalently bound. Human PI has a role in controlling tissue destruction by endogenous serine proteinases. A genetic deficiency of PI, which accounts for 90% of the trypsin inhibitory capacity in blood plasma, has been shown to be associated with premature development of pulmonary emphysema. The degradation of elastin associated with emphysema probably results from a local imbalance of elastolytic enzymes and the naturally occurring tissue and plasma proteinase inhibitors. PI rapidly inhibits human pancreatic and leukocyte elastases (*Biochem. Biophys. Res. Comm.*, Vol. 72, No. 1, pages 33-39, 1976; ibid., Vol. 88, No. 2, pages 346-350, 1979).

A number of methods have been employed to isolate PI from the blood plasma. A majority of these methods are directed to laboratory scale isolation while others pertain to production on a commercial level.

Pannell et al., *Biochemistry*, Vol. 13, pages 5439-5445, (1974), employed a process wherein albumin-poor blood plasma was pooled and fractionated with solid ammonium sulfate (0.60-0.80 saturation). The precipitate resulting was solubilized and dialyzed and applied to a column of DEAE-cellulose. The 0.05-0.15 M NaCl linear gradient is pooled, concentrated, and dialyzed, and then applied again to a column of DEAE-cellulose. The linear gradient from 0.05-0.20 NaCl was collected, pooled, and concentrated to give PI.

In the method of Saklatvala et al., *Biochem. J.,* Vol. 157, pages 339-351 (1976), human plasma was fractionated using ammonium sulfate (80% saturation) to give a precipitate, which was dissolved, dialyzed and chromatographed on DEAE-cellulose. The 0.5 M NaCl extract was applied to a concanavalin A-Sepharose column. The alpha-D-methyl glucopyranoside eluate was concentrated and applied again to a DEAE-cellulose column. The 0.0-0.2 M NaCl eluate contained PI.

Fifty percent saturated ammonium sulfate precipitation was used by Musiani et al., *Biochem.,* Vol. 15, pages 798-804 (1976) to separate a PI-rich fraction that was solubilized and then subjected to successive chromatographic steps using DEAE ion exchanger, concanavalin A-Sepharose, Sephadex G-100, and an immunoadsorbent column to yield purified PI.

A large scale purification of PI from human plasma was disclosed by Kress et al., *Preparative Biochemistry*, Vol. 3, No. 6, pages 541-552 (1973). The precipitate from the 80% ammonium sulfate treatment of human plasma was dialyzed and chromatographed on DEAE-cellulose. The concentrate obtained was again dialyzed and gel filtered on Sephadex G-100. The PI-containing fractions were chromatographed twice on DE-52 cellulose to give PI.

Glaser et al., ibid., Vol. 5, No. 4, pages 333-348 (1975) isolated PI from Cohn Fraction IV-1 in 30% overall yield. Dissolved IV-1 was chromatographed on DEAE-cellulose, QAE-Sephadex, concanavalin A-Sepharose, and G-150 Sephadex to give PI.

An integrated plasma fractionation system based on polyethylene glycol (PEG) was disclosed by Hao et al., *Proceedings of the International Workshop on Technology for Protein Separation and Improvement of Blood Plasma Fractionation,* held Sept. 7-9, 1977, Reston, Virginia. In the published method Cohn cryoprecipitate was mixed with PEG in an amount of 40 grams per liter (g/l). All operations were conducted at 5° C.

After stirring for 60 minutes, the first fraction was removed by centrifugation. An additional 60 g/l of PEG was added to the supernate (final concentration approximately 10%). Prothrombin complex (PTC) was then extracted from the 10% PEG supernate by batchwise adsorption on DEAE cellulose, and an additional 100 g/l of PEG was added to obtain the 10-20% PEG precipitate. The four fractions thus obtained were 0-4% PEG precipitate, 4-10% PEG precipitate, 10-20% PEG precipitate and 20% PEG supernate, and were designated as Fractions A, B, C and D, respectively. It should be pointed out that these PEG concentrations were based on the original volume of cryosupernate.

The distribution of proteins in the four PEG fractions was as follows: Fibrinogen was the dominant protein in Fraction A with albumin being the major contaminant. Most of the contaminating albumin in Fractions A, B and C resulted from coprecipitation and/or entrapment of supernate since albumin by itself did not precipitate under these conditions. Fraction B was rich in plasminogen, C3 component of complement, IgG and IgM. In addition, virtually all of the beta-lipoproteins were present in this fraction. Fraction C contained appreciable quantities of alpha$_2$macroglobulin, IgA and was rich in prothrombin and other coagulation factors which constitute the so-called prothrombin complex. However, the authors found that better yields of PTC could be obtained from the 10% PEG supernate rather than from the 10-20% PEG precipitate. Fraction D was dominated by albumin but also contained all of the alpha-1-acid glycoprotein as well as most of the PI, antithrombin III (AT III), ceruloplasmin ($C_p$), haptoglobin, transferrin ($T_f$) and C1 esterase inhibitor (C1 inhib.). Several additional proteins were also isolated from Fraction D including prealbumin (PA), retinol binding protein (RBP), transcortin, and angiotensinogen. In general, most of the smaller proteins were in Fraction D.

SUMMARY OF THE INVENTION

The invention described herein is a method for separating alpha-1-proteinase inhibitor from blood plasma or blood plasma fractions which contain PI. In the present method blood plasma is fractionated according to the Cohn ethanol fractionation technique or its modifications [see for example, Cohn et al., *J. Chem. Soc.,* 68, 459 (1946); Oncley et al., ibid., 71, 541 (1949); U.S. Pat. No. 2,390,074; "The Plasma Proteins", second edition, Volume III, pages 548-550, Academic Press, New York, N.Y.] to give a Cohn fraction containing PI. An aqueous solution of the PI-containing Cohn fraction is prepared, and the pH of the solution is adjusted to about 6.5-8.5. Following a hold period of about 0.2-24 hours at 2°-50° C., a polycondensed polyglycol, for example, polyethylene glycol (PEG) is added to the solution, the pH of which is then adjusted to about 4.6–5.9 to selectively precipitate unwanted proteins from the effluent in which a substantial proportion of the PI is retained. The effluent is treated to separate PI therefrom directly or with further purification.

The primary advantage of the present method is that PI may be separated from blood plasma in high yield. The PI obtained by our method has a high specific activity when compared to the product obtained by many of the methods of the prior art.

Another advantage of the invention is the ease with which the method may be applied to the separation of PI from blood plasma. The separation, in addition, can be carried out inexpensively because of the low cost of the agents employed in the present method.

An important feature of the present invention is the discovery that the concentration of PEG and subsequent pH adjustment employed have a marked effect on the ability to separate PI from the remaining proteins. If about 20% PEG is used to treat dissolved Fraction IV-1, the PI remains in solution and precipitates from the PEG supernatant by acidifying to pH 5.1–5.5. However, other proteins are also found in the precipitate that forms. Surprisingly, however, we have discovered that treatment of Fraction IV-1 with about 10–15 grams of a polycondensed polyglycol per 100 ml of Fraction IV-1 (10–15% weight/volume, w/v) results in a situation wherein the PI does not precipitate from the supernatant when the latter is acidified. Other proteins present in the supernatant do precipitate. Separation of the precipitate from the supernatant yields a PI-containing supernatant from which PI can readily be further purified.

DESCRIPTION OF THE PREFERRED EMBODIMENTS

As mentioned above, the starting material for the method of the invention is blood plasma that has been fractionated by the Cohn ethanol fractionation technique or its modifications to give a concentrate containing PI such as, among others, Cohn Fraction IV and IV-1 and includes reworks of these fractions wherein other proteins are first removed. In the following description emphasis is directed to Cohn Fraction IV-1 by way of illustration and not limitation.

Fraction IV-1 paste may be used directly or it may first be treated to remove lipids contained therein, for example, by contact with "cold" acetone, aerosil, calcium and dextran sulfate, and the like. For instance, IV-1 paste may be mixed with acetone in the proportion of about 10–40 parts of acetone per part of Fraction IV-1. The temperature during this treatment is maintained at about −30° to −35° C., the starting temperature of the cold acetone. Acetone also removes water from Fraction IV-1 paste, thereby resulting, upon removal of the acetone by conventional means, in a dry powder containing substantially all of the PI.

An aqueous solution or suspension of Fraction IV-1 paste or powder as described above is prepared by mixing Fraction IV-1 with water in the proportion of about 8–12 grams of Fraction IV-1 per 100 ml of water. At this time, the pH of the mixture is adjusted to about 6.5–8.5 by the addition of a physiologically-acceptable agent such as tris-(hydroxymethyl)aminomethane (TRIS) and the like. In addition, a physiologically-acceptable salt such as sodium chloride or the like may be added to the aqueous mixture in an amount sufficient to achieve a concentration of about 0.01–0.10 M.

It is within the compass of the invention, and preferred, to mix Fraction IV-1 with a buffer of a particular pH so that the resulting mixture will have a pH and a concentration within the ranges quoted above. As the buffer one may use TRIS hydrochloride and the like. Additionally, the buffer may contain a physiologically-acceptable salt in an amount so that its concentration in the final mixture of Fraction IV-1 and buffer will be about 0.01–0.10 M.

The above mixture is prepared at a temperature of about 2°–50° C., and then held at a temperature within the above range for a period of 0.2–24 hours. There is an inverse relationship between the time and temperature in this step. Generally, for each 10° C. rise in temperature the hold time should decrease by half with the preferred conditions being about 0.5 hour at about 45° C. or about 8 hours at about 5° C.

Following this holding period a polycondensed polyglycol, e.g., PEG, of molecular weight of about 2,000–10,000 is added to the mixture. For purposes of the invention about 10–15 grams of polycondensed glycol are used per 100 ml of the aqueous mixture containing Fraction IV-1. Usually, the amount of polycondensed glycol employed is determined by the initial amount of Fraction IV-1 paste mixed with water in the initial step in this method. Thus, if 8 grams of Fraction IV-1 were mixed with 100 ml of water, then about 10–11 g of polycondensed polyglycol should be used per 100 ml of aqueous mixture. On the other hand if 10 grams of Fraction IV-1 were initially mixed with 100 ml of water, then about 14–15 g of polycondensed polyglycol per 100 ml of aqueous mixture should be employed in this step. The relationship, therefore, between the initial amount of Fraction IV-1 and the polycondensed polyglycol is about 1 gram of glycol per about 0.5–0.8 grams of Fraction IV-1. The preferred agents and amounts in this particular step are about 11 grams of a PEG having a molecular weight of about 3,000–4,000 and about 8 grams of Fraction IV-1 per 100 ml of aqueous mixture. The mixture of polycondensed polyglycol and Fraction IV-1 may be held for a period of about 1–24 hours at a temperature of about 2°–10° C.

The precipitate that forms can be separated by conventional means such as centrifugation and discarded, and the effluent can be treated as described hereinbelow. However, it is preferred not to separate the effluent and precipitate at this time. Rather, the pH of the entire mixture is adjusted to within the range of about 4.6–5.7, preferably about 5.0–5.1, by the addition thereto of a physiologically-acceptable acid such as acetic acid, hydrochloric acid, citric acid, phosphoric acid, or the like. The acidified mixture is held for only 0–60 minutes, or generally, for as short a time as possible since the yield of active PI decreases with time. The precipitate that forms containing unwanted proteins is separated from the solution, again by conventional means such as centrifugation, and discarded.

The pH of the remaining solution is adjusted to about 5.5–8.6, preferably about 6.5, by the addition of a physiologically acceptable alkaline material such as, for example, sodium hydroxide.

The so-adjusted material is then contacted with an anion exchange medium such as DEAE-Sephadex, QAE-Sephadex, DEAE-Sephacel, DEAE-cellulose, DEAE-Sepharose or the like. A variety of conditions may be used in this particular step. Contact with the above agent may be carried out batch-wise or continuously. For best results the anion exchange medium is placed in a chromatographic column and the PI eluted therefrom. In general, the anion exchange medium is first equilibrated in a buffer solution of pH about 5.5-8.6. Next, the anion exchange medium is contacted with the above solution containing PI in the proportion of about 10-15 volumes of solution to 1 volume exchanger. The anion exchange medium is washed again with a buffer solution, usually the same buffer solution as above; the amount of this wash solution generally is about 3-10 volumes per volume of exchanger.

The PI is removed by either gradient elution or stepwise elution from the anion exchange medium by contacting it with a buffer solution of pH about 5.5-8.6 containing 0.0-0.3 M sodium chloride, 0.01-0.12 M disodium phosphate, and the like or combinations thereof.

Alternative to the use of an anion exchange medium, PI may be separated from the solution after adjustment to pH 4.6-5.4 by the addition of PEG in the amount of 10-30 g per 100 ml of solution. A precipitate containing PI is separated from the solution.

Following the separation of the solution containing PI, for example, from the anion exchange medium, the solution is treated to reduce its water content and change the ionic composition by conventional means such as by diafiltration, ultrafiltration, lyophilization, etc., or combinations thereof.

The PI concentrates can be formulated into pharmaceutical preparations for therapeutic, diagnostic, or other uses. To prepare them for intravenous administration the compositions are dissolved usually in water containing physiologically compatible substances such as sodium chloride, glycine, and the like and having a buffered pH compatible with physiological conditions. Generally, guidelines for intravenously administered compositions are established by governmental regulations.

It is desirable that the PI concentrates be non-hepatitis infective. In this respect the concentrates may be treated to reduce hepatitis infectivity by, for example, pasteurization, i.e., heating at a temperature and for a time, such as, for example, at about 60° C. or more for a period up to about 10 hours, sufficient to render the PI hepatitis non-infective. To stabilize the PI during this heat treatment a source of citrate ions is added in an amount sufficient to stabilize the PI during heating. Generally, if about 20 mg of total protein is present in the PI concentrate, then the solution is made about 0.25-0.5 M in citrate ion. The pH of the mixture during this heating step should preferably be about 6.0-7.0.

To achieve maximum stabilization of PI during heating it is desirable to use a carbohydrate as the stabilization agent either alone or with sodium citrate. For this purpose one may use as the carbohydrate a mono-, di-, and trisaccharide such as arabinose, glucose, galactose, maltose, fructose, fibose, mannose, rhammose, sucrose, etc., or a sugar alcohol such as sorbitol and mannitol, etc., in an amount of about 0.5-2.4 g/ml of PI solution.

As mentioned above the pasteurized products of the invention may be incorporated into pharmaceutical preparations which may be used for therapeutic purposes. However, the term "pharmaceutical preparation" is intended in a broader sense herein to include preparations containing a protein composition in accordance with this invention used not only for therapeutic purposes, but also for reagent or diagnostic purposes as known in the art or for tissue culture. The pharmaceutical preparation intended for therapeutic use should contain a therapeutic amount of PI, i.e., that amount necessary for preventative or curative health measures. If the pharmaceutical preparation is to be employed as a reagent or diagnostic, then it should contain reagent or diagnostic amounts of PI.

EXAMPLES

The invention described above is demonstrated further by the following illustrative examples.

Assays

PI is estimated by its elastase inhibitory capacity, using a chromogenic substrate for elastase. Hydrolysis of N-succinyl-L-alanyl-L-alanyl-L-alanyl-p-nitroanilide ($SA_3pNA$) by elastase causes an increase in absorption at 405 nm. This increase is continuously monitored usually at 37° C. Comparisons of the linear changes of absorbance with time in the presence and absence of sample (PI) are made. The amount of inhibitor is then calculated based on the known molecular weights of elastase and PI, on the known 1:1 stoichiometry, and on the known amount of elastase used.

PI may also be estimated by its trypsin inhibitory capacity in a similar manner.

EXAMPLE 1

Fraction IV-1 was obtained by means of the Cohn fractionation scheme as mentioned above.

Fraction IV-1 paste (10.0 g) was dissolved in 0.1 liter of a buffer solution of pH 8.5 containing 0.1 M (TRIS) and 0.02 M sodium chloride. The mixture was stirred for 16 hours at 5° C.

PEG 4000 (from Union Carbide Corporation) was added to a level of 14% (w/v). The mixture was stirred to dissolve the PEG and then centrifuged at 15,000×g. The supernatant was collected, diluted with 0.22 volumes of water, acidified to pH 5.1 by addition of 1 N acetic acid, and centrifuged. The supernatant containing the PI was collected and analyzed by the aforedescribed methods. The results are found in Table 1.

TABLE 1

| Sample | $A_{280}$ | PI (mg/ml) | Volume (ml) | Total PI (mg)[1] | Recovery (mg) | Purification Factor |
| --- | --- | --- | --- | --- | --- | --- |
| Fraction IV-1 solution | 30.3 | 2.0 | 110 | 220 | 100 | 1.0 |
| PEG 4000 supernatant | 12.6 | 1.9 | 110 | 209 | 95 | 2.2 |
| Acid supernatant | 4.0 | 1.4 | 129 | 180 | 82 | 5.2 |

EXAMPLE 2

The procedure of Example 1 was followed with the exception that the Fraction IV-1 in buffer solution was held for varying times prior to addition of PEG 4000. The results are tabularized below.

TABLE 2

| Holding Period (hr.) | PI in Solution (mg/ml) | PI in 14% PEG 4000 Supernatant (mg/ml) |
| --- | --- | --- |
| 0.25 | 1.9 | 0.9 |
| 1 | 1.9 | 1.0 |
| 2 | 1.9 | 1.3 |
| 4 | 1.9 | 1.4 |

TABLE 2-continued

| Holding Period (hr.) | PI in Solution (mg/ml) | PI in 14% PEG 4000 Supernatant (mg/ml) |
|---|---|---|
| 7 | 1.9 | 1.6 |
| 23 | 1.9 | 1.6 |

EXAMPLE 3

Fraction IV-1 (50 g) was dissolved in 500 ml of 0.1 M Tris buffer, pH 7.5, to which was added PEG 4000 to a level of 14% (w/v). The samples were centrifuged and the supernatants divided into four equal parts. Each part was diluted with 0.22 volumes of 0.1 M Tris buffer containing varying amounts of sodium chloride so that the final sodium chloride concentrations were 0, 0.01, 0.02, and 0.03 M. Each sample was then acidified to pH 5.2 by addition of 1 N acetic acid. The samples were centrifuged, and the supernatants were separated and adjusted to pH 7.4 by addition of acid.

The results are tabularized below.

TABLE 3

| Sample | $A_{280}$ | Volume (ml) | PI (mg/ml) | Total PI (mg) | Yield (%) |
|---|---|---|---|---|---|
| IV-1 solution | 31.3 | 545 | 1.92 | 1037 | 100 |
| PEG supernatant | 13.2 | 570 | 1.36 | 762 | 73 |
| Acid supernatant 0.03 M NaCl | 4.27 | 170 | 0.67 | 113 | 60 |
| Acid supernatant 0.02 M NaCl | 4.02 | 170 | 0.71 | 121 | 64 |
| Acid supernatant 0.01 M NaCl | 3.94 | 170 | 0.61 | 104 | 55 |
| Acid supernatant 0.00 M NaCl | 4.00 | 170 | 0.60 | 102 | 54 |

EXAMPLE 4

PI acid supernatant was prepared according to the procedure of Example 1; 1300 ml of this supernatant was combined with 650 ml of water and placed on a 100 ml column of DEAE-Sephacel equilibrated with 0.01 M sodium phosphate at pH 6.5. After the column was washed with one column volume of 0.01 M sodium phosphate, the column was eluted with a linear gradient to 0.12 M sodium chloride (total volume of wash was 1.5 l). The active fractions were combined.

The above manipulations were repeated using DEAE-Sepharose as the anion exchanger medium in place of DEAE-Sephacel and also repeated using 0.12 M disodium phosphate as the eluting medium. The results are summarized below.

TABLE 4

| Anion Exchange Medium | Eluting Medium | Specific Activity (mg/ml/$A_{280}$) | PI Yield (%) |
|---|---|---|---|
| DEAE-Sephacel | sodium chloride | 0.98 | 64 |
| DEAE-Sepharose | sodium chloride | 1.12 | 63 |
| DEAE-Sepharose | disodium phosphate | 1.30 | 83 |

EXAMPLE 5

PI acid supernatant was prepared according to the procedure of Example 1; 1300 ml of this supernatant was combined with 650 ml water-for-injection (WFI), and 100 ml of anion exchange medium, and buffered with 0.01 M sodium phosphate, 0.05 M sodium chloride, pH 6.5. The mixture was stirred for 1 hour and allowed to settle. After filtration, the medium was washed five times with 250 ml of the above buffer and then was eluted by treatment with 250 ml of the above buffer at 0.15 M sodium chloride (five washes). The results are summarized below.

TABLE 5

| Anion Exchange Medium | PI Yield (%) | Purification Factor |
|---|---|---|
| DEAE-Sephadex A-50 | 80 | 2.1 |
| Whatman DE-52 Cellulose | 44 | 1.8 |
| QAE-Sephadex | 71 | 1.6 |
| Phoenix DEAE-Cellulose | 55 | 1.8 |

EXAMPLE 6

PI supernatant was prepared according to the procedure of Example 5 and was concentrated by means of hollow fiber ultrafiltration to a concentration of 10 mg PI/ml of supernatant. The pH was adjusted to 7 or 6.5. Aliquots of this concentrated material were taken and mixed with a stabilizer or not as summarized in the Table below. The aliquots were then heated at 60° C. for 10 hours. The results appear in the following Table.

TABLE 6

| Sample | pH | PI % Recovery |
|---|---|---|
| 0.5 M sodium citrate | 7 | 58 |
| 0.5 M sodium citrate | 6.5 | 90 |
| 1.2 g/ml sucrose | 7 | 100 |
| 0.5 M sodium citrate + 0.8 g/ml sucrose | 6.5 | 100 |
| no stabilizer | 7 | 12 |

We claim:

1. A method for separating alpha-1-proteinase inhibitor from a blood plasma fraction containing the same, which comprises the steps of
   (a) holding an aqueous solution of the blood plasma fraction at a pH of about 6.5–8.5, and a temperature of about 2°–50° C. for a period of about 0.2–24 hours,
   (b) mixing the solution with a polycondensed polyglycol in the proportion of about 10–15 grams of polyglycol per 100 ml of aqueous solution containing the blood plasma fraction and adjusting the pH of the mixture to about 4.6–5.7 to selectively precipitate unwanted proteins from the solution without precipitation of alpha-1-proteinase inhibitor, and
   (c) separating alpha-1-proteinase inhibitor from the solution.

2. The method of claim 1 wherein 1 part of polyglycol is used per 0.5–0.8 parts of blood plasma fraction.

3. The method of claim 1 wherein the mixture of the solution with the polyglycol is held at a temperature of about 2°–10° C. for a period of about 1–24 hours prior to the adjustment of the pH of the mixture.

4. The method of claim 1 which further includes the step of treating the alpha-1-proteinase inhibitor to render it hepatitis non-infective.

5. The method of claim 4 wherein the alpha-1-proteinase inhibitor is rendered hepatitis non-infective by heating an aqueous solution of the alpha-1-proteinase inhibitor in the presence of a heat stabilizing agent for a time and at a temperature and pH sufficient to render the alpha-1-proteinase inhibitor hepatitis non-infective.

6. The method of claim 5 wherein the heat stabilizing agent is a source of citrate ions.

7. The method of claim 5 wherein the heat stabilizing agent is a carbohydrate.

8. The method of claim 5 wherein the heat stabilizing agent is a mixture of a carbohydrate and a source of citrate ions.

9. The method of claim 5 wherein the alpha-1-proteinase inhibitor is heated for about 60° C. or more for a period up to about 10 hours at a pH of about 6.0–7.0.

10. The method of claim 1 wherein an effluent solution is separated from a precipitate in Step b prior to adjusting the pH of the mixture.

11. The method of claim 1 wherein the alpha-1-proteinase inhibitor is separated from the solution in Step c by (d) separating a supernatant solution containing alpha-1-proteinase inhibitor from a precipitate, (e) contacting the solution with an anion exchange medium at a pH of about 5.5–8.6, and (f) selectively separating an effluent containing alpha-1-proteinase inhibitor from the anion exchange medium.

12. The method of claim 11 wherein the effluent of Step f is treated to reduce its water content.

13. The method of claim 1 wherein the blood plasma fraction containing alpha-1-proteinase inhibitor is selected from the group consisting of Cohn Fraction IV-1, Cohn Fraction IV, and their reworks.

14. The method of claim 1 wherein the alpha-1-proteinase inhibitor is separated from the mixture in Step e by contacting the mixture with a polycondensed polyglycol and separating an effluent therefrom containing alpha-1-proteinase inhibitor.

15. The method of claim 1 wherein the polycondensed polyglycol is polyethylene glycol.

16. The method of claim 15 wherein the molecular weight of the polyethylene glycol is about 3000–4000.

* * * * *

UNITED STATES PATENT AND TRADEMARK OFFICE
CERTIFICATE OF CORRECTION

PATENT NO. : 4,379,087
DATED : April 5, 1983
INVENTOR(S) : MICHAEL H. COAN and WILLIAM J. BROCKWAY It is certified that error appears in the above-identified patent and that said Letters Patent are hereby corrected as shown below:

Column 2, line 61, correct "J. Chem. Soc., 68," to recite --J. Am. Chem. Soc., 68,--;

Column 3, line 50, correct "aerosil" to recite --Aerosil®--;

Column 7, line 20, correct "acid" to recite --alkali--; and

Column 10, claim 14, line 3, correct "Step e" to recite --Step c--.

Signed and Sealed this

Eighth Day of November 1983

[SEAL]

Attest:

Attesting Officer

GERALD J. MOSSINGHOFF
Commissioner of Patents and Trademarks